(12) United States Patent
Keller

(10) Patent No.: US 10,070,989 B2
(45) Date of Patent: Sep. 11, 2018

(54) CAPSULOTOMY CARTRIDGE

(71) Applicant: Mynosys Cellular Devices, Inc., Fremont, CA (US)

(72) Inventor: Christopher Guild Keller, El Cerrito, CA (US)

(73) Assignee: Mynosys Cellular Devices, Inc., Fremont, CA (US)

( * ) Notice: Subject to any disclaimer, the term of this patent is extended or adjusted under 35 U.S.C. 154(b) by 666 days.

(21) Appl. No.: 14/613,112

(22) Filed: Feb. 3, 2015

(65) Prior Publication Data

US 2015/0216728 A1 Aug. 6, 2015

Related U.S. Application Data

(60) Provisional application No. 61/937,817, filed on Feb. 10, 2014, provisional application No. 61/935,271, filed on Feb. 3, 2014.

(51) Int. Cl.

| A61B 18/18 | (2006.01) |
|---|---|
| A61F 9/007 | (2006.01) |
| A61B 18/08 | (2006.01) |
| A61B 18/14 | (2006.01) |
| A61B 18/00 | (2006.01) |

(52) U.S. Cl.
CPC ........ *A61F 9/00754* (2013.01); *A61B 18/082* (2013.01); *A61B 2018/00321* (2013.01); *A61B 2018/00601* (2013.01); *A61B 2018/00625* (2013.01); *A61B 2018/1407* (2013.01); *A61B 2018/1465* (2013.01); *A61B 2218/007* (2013.01)

(58) Field of Classification Search
CPC .............. A61F 9/00754; A61B 18/082; A61B 2018/00321; A61B 2018/00601; A61B 2018/00625; A61B 2018/1465; A61B 2218/007
See application file for complete search history.

(56) References Cited

U.S. PATENT DOCUMENTS

| 4,301,802 A | 11/1981 | Poler |
| 4,570,632 A | 2/1986 | Woods |
| 5,269,787 A | 12/1993 | Cozean, Jr. et al. |
| 5,345,935 A | 9/1994 | Hirsch et al. |
| 5,346,491 A | 9/1994 | Oertli |
| 5,423,330 A | 6/1995 | Lee |

(Continued)

FOREIGN PATENT DOCUMENTS

| JP | 2008-155038 A | 7/2008 |
| WO | WO 1999/060936 | 12/1999 |

(Continued)

*Primary Examiner* — Lindsey G Wehrheim
(74) *Attorney, Agent, or Firm* — Fenwick & West LLP

(57) ABSTRACT

A cartridge of a surgical device is disclosed that includes a capsulotomy device and a shell structure. The capsulotomy device includes a suction cup, a chamber configured to provide suction to the suction cup, and a cutting element that can be put into contact with a lens capsule of an eye to excise a portion of tissue of the lens capsule. Both the suction cup and cutting element are collapsible. The shell structure is configured for housing the capsulotomy device. The housing of the shell structure can contain the suction cup, the chamber, and the cutting element of the capsulotomy device to protect the device before it is used in performing a capsulotomy.

21 Claims, 12 Drawing Sheets

(56) References Cited

U.S. PATENT DOCUMENTS

| | | |
|---|---|---|
| 5,423,841 A | 6/1995 | Kornefeld |
| 5,470,352 A | 11/1995 | Rappaport |
| 5,569,280 A | 10/1996 | Kamerling |
| 5,624,392 A | 4/1997 | Saab |
| 5,669,923 A | 9/1997 | Gordon |
| 5,860,994 A | 1/1999 | Yaacobi |
| 5,873,883 A | 2/1999 | Cozean, Jr. et al. |
| 5,972,011 A | 10/1999 | Pierce et al. |
| 6,066,138 A | 5/2000 | Sheffer et al. |
| 6,165,190 A | 12/2000 | Nguyen |
| 6,306,155 B1 | 10/2001 | Chandler et al. |
| 6,551,326 B1 | 4/2003 | Van Heugten et al. |
| 6,629,980 B1 | 10/2003 | Eibschitz-Tsimhoni |
| 6,758,857 B2 | 7/2004 | Cioanta et al. |
| 6,887,261 B1 | 5/2005 | Peyman |
| 7,011,666 B2 | 3/2006 | Feinsod |
| 8,137,344 B2 | 3/2012 | Jia et al. |
| 8,162,931 B2 | 4/2012 | Ben-Nun |
| 8,235,978 B2 | 8/2012 | Ben-Nun |
| 8,657,813 B2 | 2/2014 | Ben-Nun et al. |
| 8,702,698 B2 | 4/2014 | Keller |
| 2004/0010284 A1 | 1/2004 | Maloof et al. |
| 2004/0092982 A1 | 5/2004 | Sheffer |
| 2004/0106929 A1 | 6/2004 | Masket |
| 2004/0260254 A1 | 12/2004 | Neilson et al. |
| 2005/0165346 A1 | 7/2005 | Neilson et al. |
| 2005/0171531 A1 | 8/2005 | Eliachar et al. |
| 2006/0009782 A1 | 1/2006 | Brown |
| 2006/0100617 A1 | 5/2006 | Boukhny |
| 2006/0105309 A1 | 5/2006 | Stoll et al. |
| 2006/0195076 A1 | 8/2006 | Blumenkranz et al. |
| 2006/0254912 A1 | 11/2006 | Nussinovitch |
| 2006/0259053 A1 | 11/2006 | El-Mansoury |
| 2006/0264990 A1 | 11/2006 | Michelson et al. |
| 2006/0271188 A1 | 11/2006 | Brown |
| 2007/0049957 A1 | 3/2007 | Benitez et al. |
| 2007/0173811 A1 | 7/2007 | Couture et al. |
| 2007/0191862 A1 | 8/2007 | Ellis |
| 2007/0287999 A1 | 12/2007 | Malecki et al. |
| 2008/0015488 A1 | 1/2008 | Tu et al. |
| 2011/0071524 A1* | 3/2011 | Keller ............... A61F 9/00736 606/45 |
| 2011/0118734 A1 | 5/2011 | Auld et al. |
| 2013/0197548 A1 | 8/2013 | Keller |
| 2014/0074088 A1 | 3/2014 | Ben Nun et al. |
| 2014/0207137 A1 | 7/2014 | Keller |
| 2014/0350554 A1 | 11/2014 | Keller |

FOREIGN PATENT DOCUMENTS

| | | |
|---|---|---|
| WO | WO 2001/056519 A1 | 8/2001 |
| WO | WO 2002/043632 A1 | 6/2002 |
| WO | WO 2003/022191 A1 | 3/2003 |
| WO | WO 2004/017877 A1 | 3/2004 |
| WO | WO 2005/082302 A1 | 9/2005 |
| WO | WO 2007/120775 A2 | 10/2007 |
| WO | WO 2009/140414 A1 | 11/2009 |
| WO | WO 2014/047478 A1 | 3/2014 |

\* cited by examiner

Fig. 7
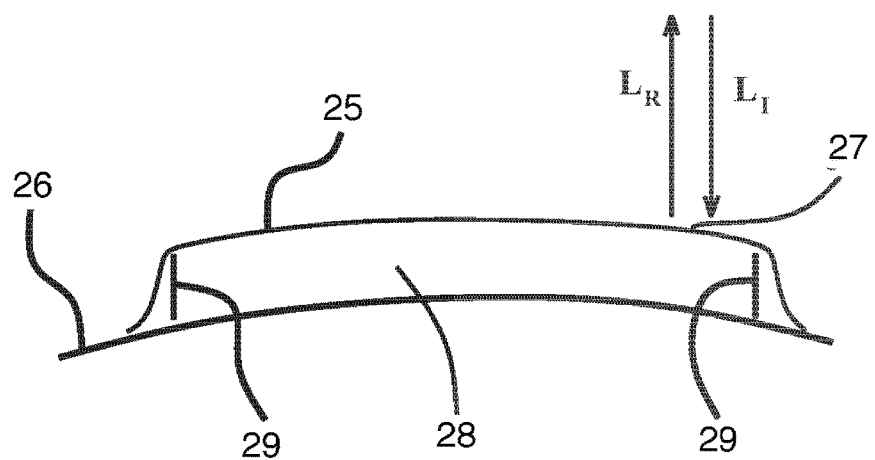
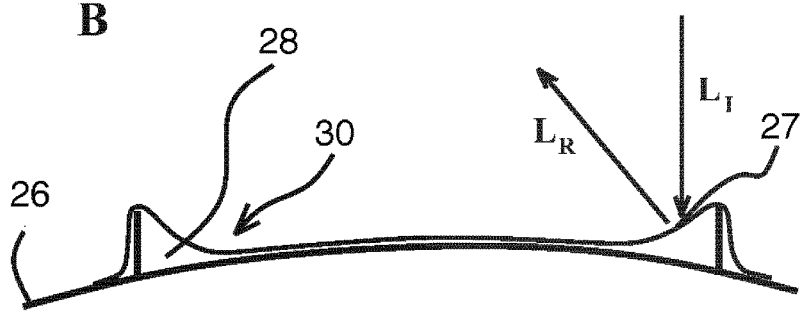

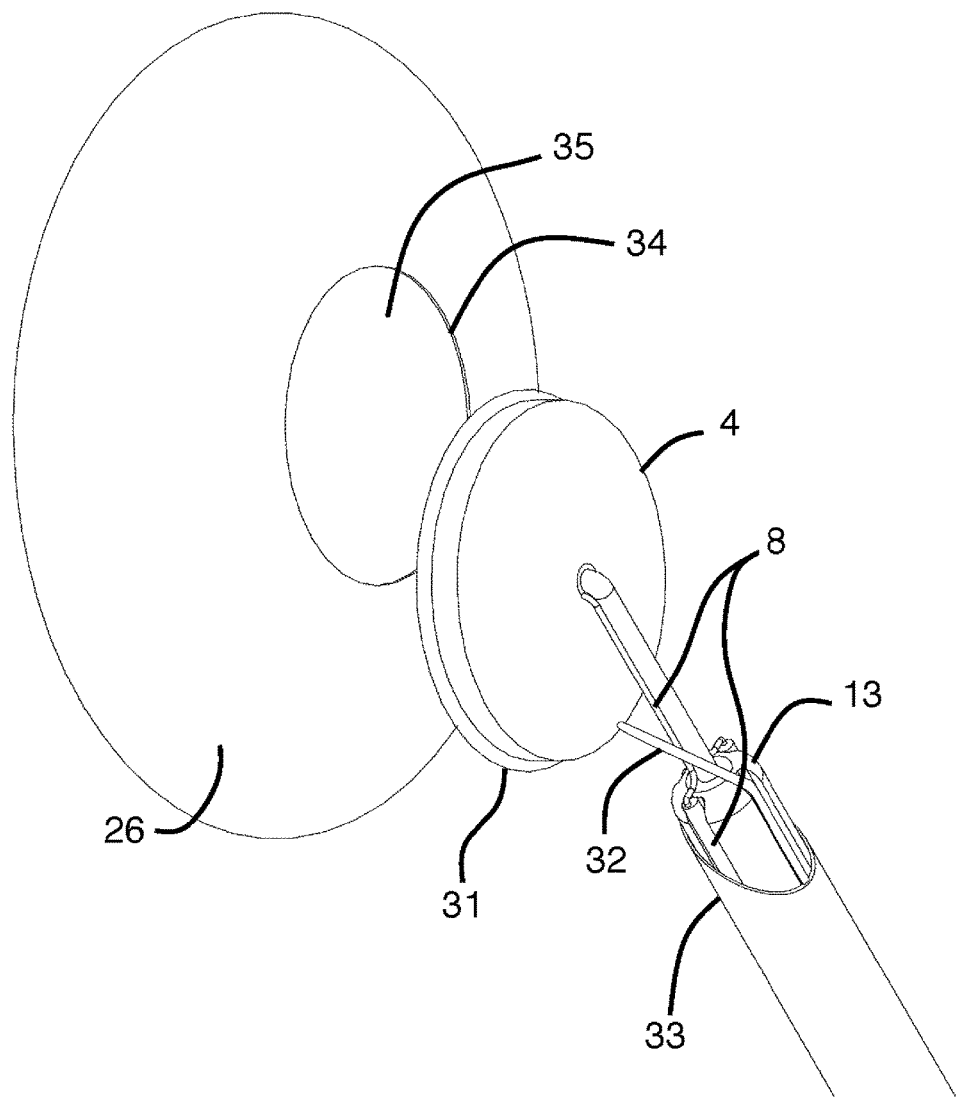

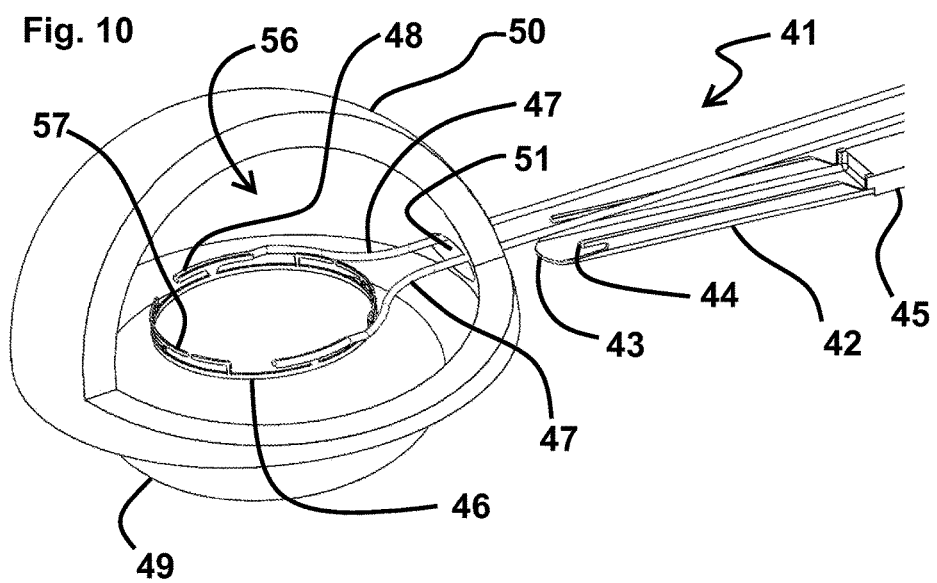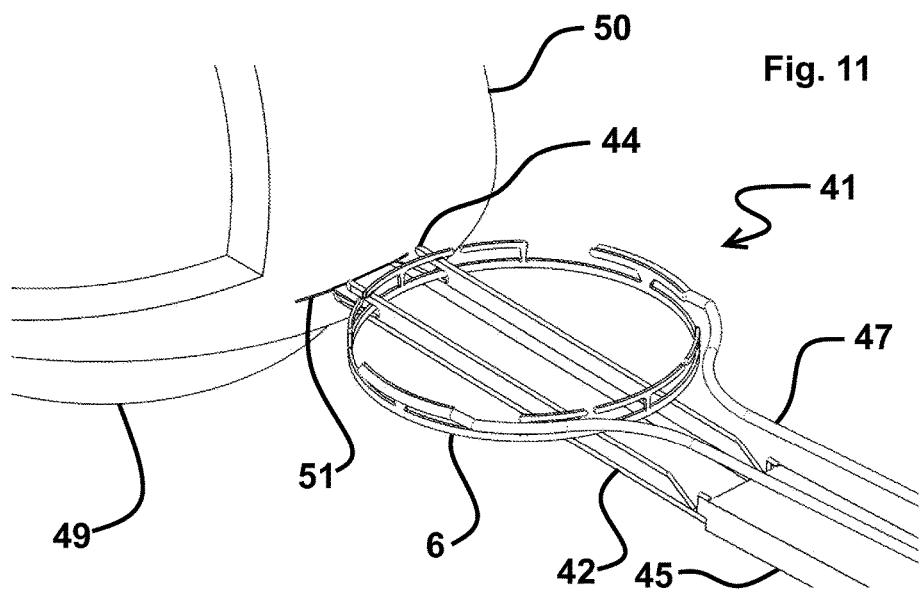

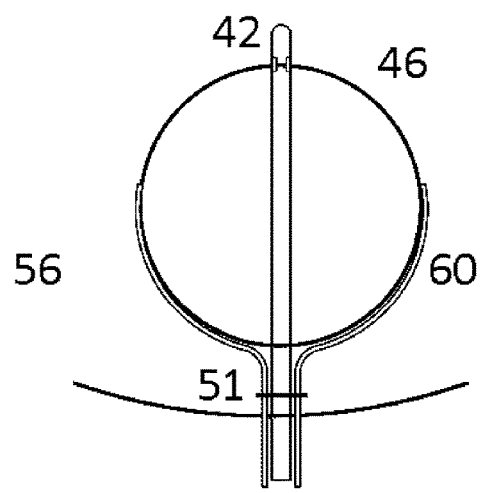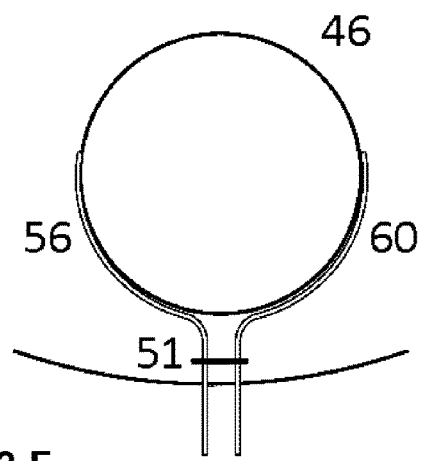
FIG. 12 E       FIG. 12 F

CAPSULOTOMY CARTRIDGE

CROSS-REFERENCE TO RELATED APPLICATIONS

This application claims the benefit of U.S. Provisional Application No. 61/935,271, filed on Feb. 3, 2014, entitled "Corneal Incision Finder," and of U.S. Provisional Application No. 61/937,817, filed on Feb. 10, 2014, entitled "Capsulotomy Cartridge," the entire disclosures of which are hereby incorporated by reference herein, including any appendices or attachments thereof, in their entirety for all purposes.

STATEMENT REGARDING FEDERALLY SPONSORED RESEARCH

This invention was made with government support under grant nos. 5R44EY021023-03, 2R44EY021023-04, 2R44EY021023-02, and 3R44EY021023-0351, awarded by the National Institutes of Health. The government has certain rights in the invention.

BACKGROUND

This invention relates generally to microsurgery of the eye, and more specifically to lens cataract surgery.

Opacification of lens material resulting in a cataract is a significant worldwide cause of visual disability. Vision can be restored by the removal of the cataractous lens using a procedure involving phacoemulsification and aspiration of the lens fragments from the eye. Prior to phacoemulsification, an opening called a capsulotomy is first made in the lens capsule that encases the lens. An ideal capsulotomy is round, visually centered, and of a prescribed diameter to fit the clinical need. A capsulotomy with these characteristics is difficult to achieve consistently with manually operated capsulorhrexis instruments.

While certain devices are capable of performing capsulotomies, more convenient and sterile surgical devices and methods for performing capsulotomies are desirable.

SUMMARY

Embodiments of the invention provide a cartridge of a surgical device. The cartridge includes a capsulotomy device and a shell structure. The capsulotomy device comprises a suction cup, a chamber in fluid communication with the suction cup and configured to provide suction to the suction cup via a suction mechanism operable through a handpiece, and a cutting element that is coupled to the suction cup and can be put into contact with a lens capsule of an eye to excise a portion of tissue of the lens capsule. Both the suction cup and cutting element are collapsible. The shell structure is configured for housing the capsulotomy device, and includes a housing having an outer surface configured to contain the suction cup, the chamber, and the cutting element of the capsulotomy device to protect the device before use in performing a capsulotomy. The cartridge is positionable on the handpiece so that suction is provided to the suction cup via the suction mechanism when the surgical device is in use for performing the capsulotomy.

In some embodiments, the cartridge is reversibly attachable to the handpiece of the surgical device. In other embodiments, the cartridge also includes a suction generator coupled to the chamber that is configured to be actuated to expand the chamber to create the suction provided to the suction cup. In an embodiment, the cutting element includes a cutting ring coupled to one or more electrical leads extendable from the cartridge and through the handpiece. For example, the cutting ring can be coupled to a first electrical lead and a second electrical lead, the two leads located 180 degrees apart from each other around an edge of the cutting ring.

In an embodiment, the cartridge also includes a handle coupled to the suction cup and including a slidable member, and a tether coupled to the slidable member of the handle and to the suction cup, such that the tether is in a slack position when the suction cup is sealed against a lens capsule of an eye, and in a taut position when a portion of tissue of the lens capsule has been excised by the cutting element. In another embodiment, the shell structure includes an incision finder that has a leading edge and one or more hooks. The leading edge is configured for insertion through a corneal incision in the eye into an anterior chamber, and the hooks are configured to reversibly attach to the cutting element and pull the cutting element through the corneal incision to the anterior chamber.

BRIEF DESCRIPTION OF THE DRAWINGS

FIG. 7 illustrates an optical technique for using deflection of the suction cup to verify suction status, according to an embodiment of the invention.

FIG. 9 illustrates a suction cup/cutting element readied to be removed from the eye after having excised a patch of capsular membrane, according to an embodiment of the invention.

FIG. 10 illustrates a capsulotomy device including an incision finder, according to an embodiment of the invention.

FIG. 11 illustrates a leading edge of a capsulotomy device including an incision finder, according to an embodiment of the invention.

Figure 1:
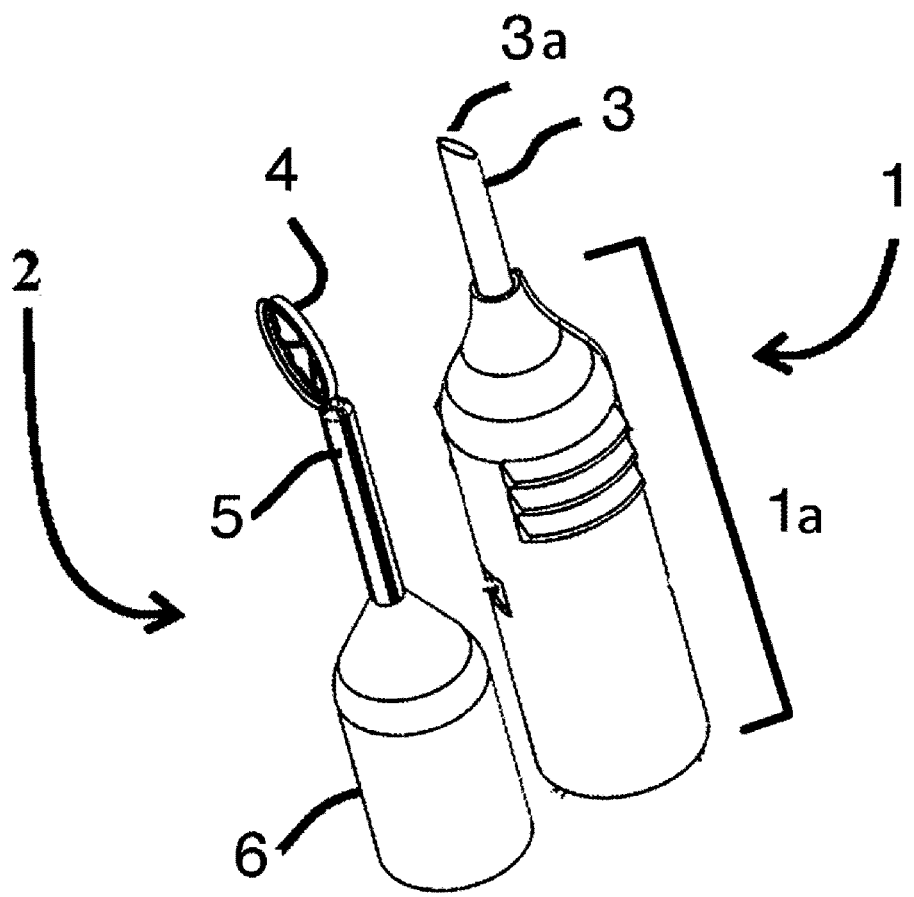
FIG. 1 illustrates components of a capsulotomy cartridge, according to an embodiment of the invention.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Embodiments of the invention are described in the context of a lens capsule surgery in which a portion of the anterior surface of a lens capsule is cut. The technique may be used for performing a treatment for cataracts in which the lens located within the capsule is removed from the eye. Moreover, the techniques and devices described herein may be useful tools for performing other medical procedures (such as corneal surgeries or surgeries involving tissue other than that in the eye). The methods and devices described throughout will describe in the context of lens capsulotomy for illustration, and the methods and devices will be referred to as capsulotomies and capsulotomy devices and capsulotomy cartridges, respectively. However, it is to be understood that the methods and devices are not limited to capsulotomy and can be used for other medical procedures.

Capsulotomy Cartridge

The surgical device described throughout provides a number of benefits. As one example, this suction-assisted capsulotomy device is produced as a reversibly attachable unit that is attached to a handpiece manipulated by a surgeon. An external shell of the cartridge is designed to fit over the capsulotomy device of the cartridge, the capsulotomy device used to perform the capsulotomy. The external shell can help ensure that the capsulotomy device remains sterile and undamaged until the procedure occurs. The cartridge can be attached to and detached from the handpiece, as is shown in the Figures that will be described below. This convenient design allows the operator (e.g., physician) of the device potentially dispose of this portion of the surgical device following the procedure, such that a new, sterile capsulotomy cartridge can be attached. This improves the surgical device from a hygienic standpoint and ensures sterility of the portions of the surgical device that will come into contact with the eye.

In some cases, the operator of the surgical device may wish to remove certain fluids during the procedure. The patient fluids may be aspirated through the suction cup to be contained within the disposable unit (e.g., the capsulotomy device and possibly also the external shell) and will not contaminate the handpiece. In addition, actuation mechanisms can be situated in the handpiece to engage appropriate features in the disposable unit to cause suction to be generated. The capsulotomy device also allows the operator of the device to determine when an appropriate level of suction is reached that is sufficient for the capsule cutting to occur. Until a sufficient level of suction is reached, a cutting element of the capsulotomy device cannot be activated to excise a portion of a lens capsule of the eye and perform a complete capsulotomy. Following the capsulotomy, the suction-assisted capsulotomy device may be removed reliably from the eye. The operator can easily use the handpiece to manipulate and withdraw the device.

FIG. 1 illustrates components of a capsulotomy cartridge that houses internal components, such as a suction cup and cutting element. In some embodiments, the capsulotomy cartridge is a disposable unit that can be attached and detached from a handpiece. Specifically, FIG. 1 shows the external shell 1 of the cartridge and the capsulotomy device 2 with self-contained suction, which fits inside the external cartridge shell 1. The external cartridge shell 1 includes a housing 1a and an inserter tip 2, the inserter tip including an opening 3a on a distal end of the inserter tip. The housing 1a of the external shell 1 thus fits over the capsulotomy device 2 such that the suction cup 4 can be contained within, such as within the inserter tip 2. The suction cup 4 and other components of the capsulotomy device 2 can thus be protected and contained in a sterile manner within the external shell 1 of the cartridge.

The external shell 1 may contain an inserter tip 3, which can be inserted through a corneal incision. The capsulotomy device 2 with self-contained suction can include a suction cup 4, a suction tube 5 within a handle (or elsewhere), and an expandable chamber 6 in fluid communication with the suction cup, for creating suction. In some embodiments, a component other than the expandable chamber and suction tube generates and provides suction to the suction cup. In some embodiments, the suction cup 4 is collapsible to a small cross section so that it can be inserted through a corneal incision (e.g., an incision of less than 3.0 mm in length). For example, the suction cup 4 can collapse to fit inside of the inserter tip 3 and can be manipulated such that the suction cup exits out of the opening 3a of the inserter tip 3. If the inserter tip 3 is positioned in a corneal incision, the suction cup can thus exit the opening 3a on the internal side of the cornea, in the anterior chamber of the eye. In some embodiments, the inserter tip 3 is a closed tip or has a cover or plug to maintain sterility. In other embodiments, the tip 3 is a closed structure and the external shell 1 is intended to be removed before use for insertion of the suction cup through the corneal incision. In this case, another device may be used to assist with the insertion of the suction cup through the corneal incision, such as a corneal incision finder that is described below, an insertion tube, or some other inserter.

The suction cup 4 can be made of an elastomeric material such as silicone or polyurethane (e.g., made by casting or by injection molding), though other materials can be used as well. The thinner the walls are, the stiffer (higher durometer) the material can be. The size range for the suction cup would commonly range from about 4.5 mm to about 7 mm in diameter, while the height would commonly range from about 0.5 mm to about 1.5 mm. However, other suction cup sizes and designs are possible. After insertion into the anterior chamber of the eye, the device is designed to rapidly return to its circular shape. The suction cup 4 generally has a roof and an underside. Different designs of a suction cup are illustrated in U.S. Pat. No. 8,702,698, U.S. Pat. App. Pub. No. 2013/0197548, U.S. Pat. App. Pub. No. 2014/0207137, U.S. patent application Ser. No. 14/353,220, and Int'l Pat. App. No. PCT/US2013/060988, which are hereby incorporated by reference herein in their entireties. Any of these designs can be used with the devices described herein.

While FIG. 1 and the other Figures herein illustrate one or more devices with a suction cup, in some embodiments the suction cup can be some other type of collapsible member that does not necessarily use suction and that is not necessarily cup-like in design. In further embodiments, there is no suction cup at all.

Figure 2:
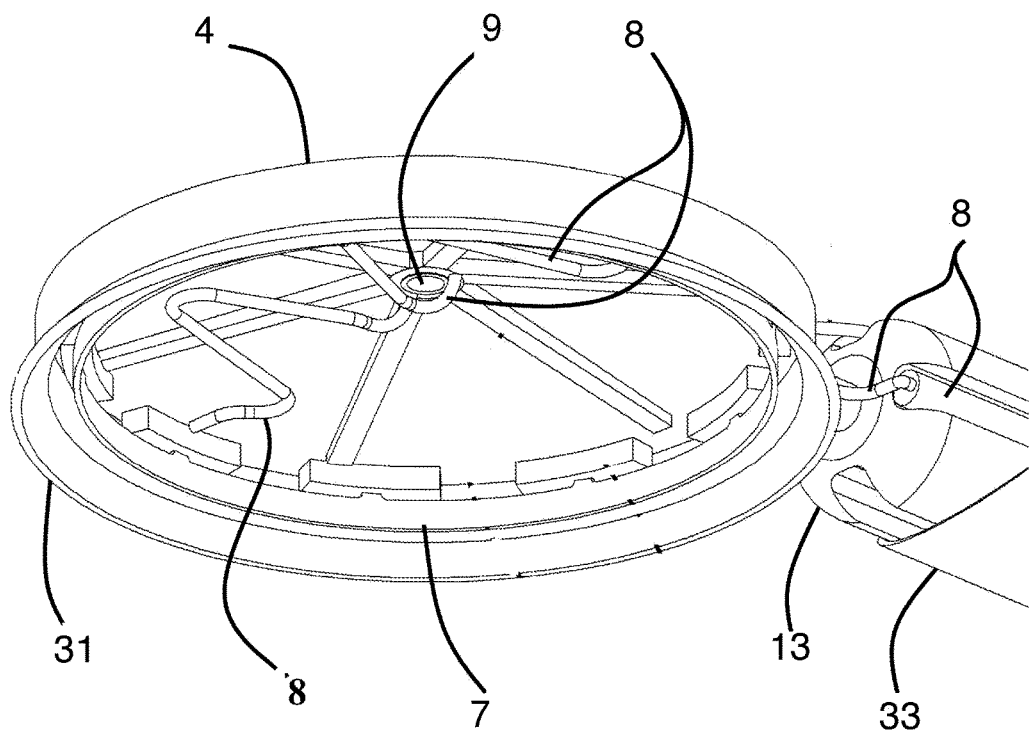
FIG. 2 illustrates the bottom view of the suction cup, connection to suction tube, the cutting element, electrical leads, and handle of a capsulotomy device, according to an embodiment of the invention.

FIG. 2 illustrates an underside of a suction cup roof of a capsulotomy device after it has been pushed through the inserter 33 (which can be the same as the inserter tip 3 of FIG. 1 or a different type of inserter) via the handle 13, according to an embodiment. Specifically, FIG. 2 shows the underside of the capsulotomy device, depicting a relationship between a cutting element 7 and the suction cup 4. In this embodiment, the cutting element 7 is attached to the underside of the suction cup roof, for example via silicone potting. The attachment is generally present at the top of the cutting element, leaving the bottom edge of the cutting element free from potting and able to come into direct contact with the lens capsule. The attachment also results in the cutting element being located concentric to the larger suction cup.

In the embodiment shown in FIG. 2, the cutting element 7 is an electrical cutting element, though other cutting element designs are also possible, such as a mechanical cutting element with a sharp edge. The anchored electrical leads 8 are visible in FIG. 2, and are attached to the cutting ring 180 degrees apart, though other designs and positions of the electrical leads are also possible.

In other embodiments, the cutting element 7 can be mounted elsewhere on the suction cup other than what is shown in FIG. 2, or mounted elsewhere on the capsulotomy device in relation to the suction cup. The cutting element 7 is configured to cut a portion of tissue (e.g. of the lens capsule). In FIG. 2, the cutting element 7 is a circular shape, but in other embodiments the cutting element can be rounded, elliptical, square, rectangular, irregular, or a different shape. The suction cup similarly can take on these shapes as well. The cutting element 7, like the suction cup 4, is collapsible. Thus, the cutting element 7 is composed of a conductive, collapsible material (e.g., nitinol or other shape-memory alloys) that can collapse for entry into the eye through the corneal incision, but can generally regain its shape prior to collapsing once it is inside the anterior chamber of the eye on the internal side of the cornea, allowing it to be used to cut or create an opening in the lens capsule of the eye.

In use, suction is delivered via the suction tube 5 that is connected to the roof of the suction cup via an opening 9 in the roof. The opening 9 could be positioned in other locations on the suction cup 4, as well. Suction applied via the suction tube 5 evacuates the contents encompassed by the suction cup 4. This causes the suction cup 4 to push up against the lens capsule to form a vacuum seal with the sealing lip 31 of the suction cup 4 positioned against the lens capsule, thereby securing the suction cup against the lens capsule. In doing so, the suction cup 4 brings the bottom edge of the cutting element 7 into close contact with the lens capsule such that the entire 360 degrees of the cutting element 7 is in contact with the lens capsule. The electrical current following device discharge enters via one of the leads 8 attached at one location to the cutting element. When the cutting element 7 cuts a patch of the lens capsule, suction applied via the suction tube 5 can be used to retain the cut portion of tissue inside the capsulotomy device during removal of the device from the eye.

As explained above, in embodiments in which there is no suction cup included, the cutting element 7 is composed of a material that is sufficiently flexible such that it can be rested against the lens capsule and provide a uniform circular cut along the circumference of the cutting element 7 without requiring suction to secure the cutting element against the lens capsule. In some embodiments, the cutting element 7 includes a coating or other structure along all or part of its surface to allow it to better adhere to the lens capsule to provide a uniform cut.

Figure 3:
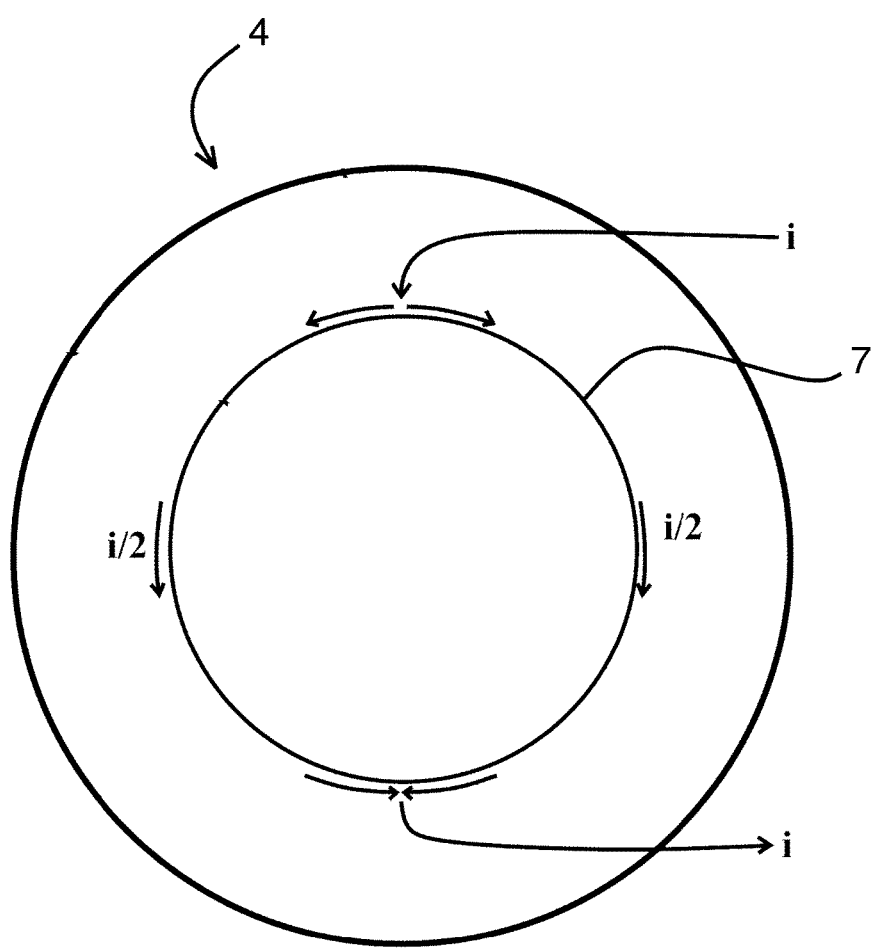
FIG. 3 illustrates the current flow entering at one lead; flow around the ring and out the other lead within the cutting element, according to an embodiment of the invention.

FIG. 3 shows the path of electrical current flow (i) within the cutting element 7 and housed within the suction cup 4 while the cutting element 7 cuts a patch of the lens capsule during a capsulotomy, according to an embodiment. Upon entering the cutting element 7 via the leads 8, one half of the current (i/2) travels along one half of the cutting element 7, while the other half of the current (i/2) travels in the other half of the cutting element 7. Current then exits the cutting element 7 at the other lead located 180 degrees away. Due to the electrical resistance of the cutting element 7, current flow causes a rapid increase in temperature in the cutting element 7. This in turn converts the water molecules near to or trapped between the bottom edge of the cutting element 7 and the lens capsule into vapor that expands rapidly and mechanically fracture the lens capsule along the precise path dictated by the size and shape of the bottom edge of the cutting element 7, which excises a piece of the lens capsule. This mechanical capsule cutting is assisted by the suction, which places tensile stress on the capsule, allowing the additional force delivered by rapid vapor generation to efficiently perform capsule cuttingScanning electron microscopy was used to examine the cuts resulting from this suction cup/cutting element combination, and shows a very smooth surface without any sign of tissue burning, consistent with mechanical cutting rather than chemical tissue burning.

A very short electrical pulse will cause the rapid increase in temperature in the cutting element (e.g., to greater than 500° C., such as 600° C., 700° C., 800° C., 900° C., 1000° C., 1200° C., 1500° C., and so forth). In some embodiments, the heating process lasts for a few microseconds (e.g., 10 microseconds or less), though heating times can differ in other embodiments (e.g., 1 microsecond, 5 microseconds, 10 microseconds, 20 microseconds, 1 millisecond, 5 milliseconds, etc.).

Figure 4:
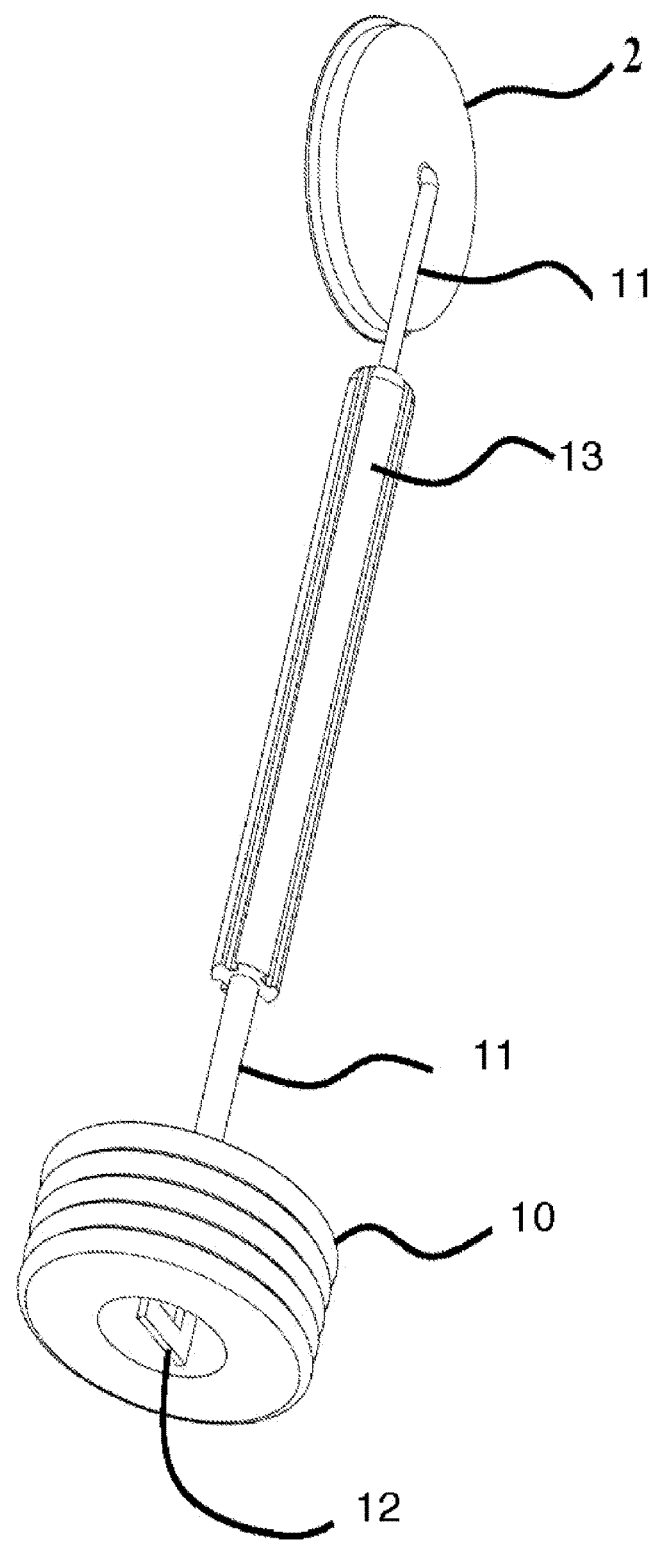
FIG. 4 illustrates a fluidically isolated suction system of a capsulotomy cartridge, according to an embodiment of the invention.

FIG. 4 illustrates a fluidically isolated or contained suction system of a capsulotomy cartridge, according to an embodiment of the invention. Specifically, FIG. 4 shows a self-contained suction system attached to the capsulotomy suction cup/cutting element. The suction system includes an expandable unit 10, such as a flexible bulb (whose volume can be changed to change the internal pressure) at one end, which may act similarly to a pipette. Another example of an expandable unit is a piston structure that slides within a tight fitting chamber. The suction tube 11, connected to the suction cup at one end is connected to the expandable chamber 10 at the other end. The suction tube 11 may run within a handle 13 that provides grooves to contain electrical leads. In another embodiment, the suction tube 11 does not run within the handle 13 but is instead coupled to an external device that generates suction. The external device can generate suction or reverse suction and apply positive pressure to the suction cup. Positive pressure can be applied to aid the suction cup in detaching from the lens of an eye after a capsulotomy is performed.

To apply suction, the suction generator, or suction puller 12 is pulled back in the direction away from the suction cup. This expands the expandable chamber 10 (for example a flexible bulb, piston chamber, or bellows) to create a vacuum, or suction. The low pressure draws in material through the lumens of tubes 11 so that material (ocular fluids or other surgical fluids in the anterior chamber) is drawn from the space between the roof of the suction cup and the lens causing sealing of the suction cup against the capsule. In an embodiment, the suction generator 12 is located within a handpiece of the capsulotomy device, the handpiece configured to reversibly attach to the capsulotomy cartridge. A self-contained suction system ensures that there is little risk of patient-to-patient contamination as all surgical fluids and debris are trapped within the expandable chamber and do not contaminate the handpiece. In some embodiments, all components that come into contact with the patient or material from the patient are single use disposable components.

Figure 5:
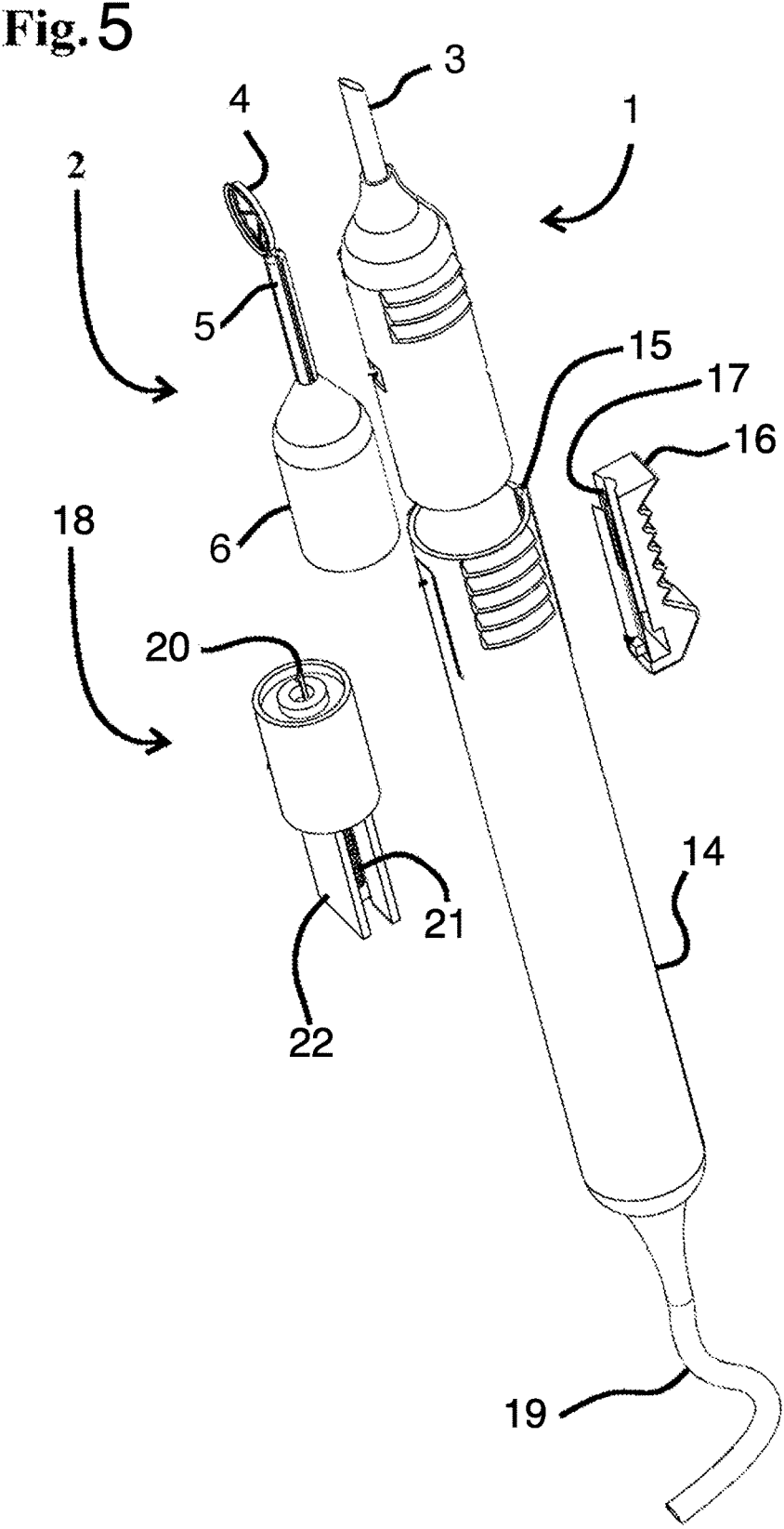
FIG. 5 illustrates the relationship between the components of the capsulotomy cartridge and the components of the handpiece, according to an embodiment of the invention.

FIG. 5 shows the relationship between the cartridge shell 1, the capsulotomy device with self-contained suction 2, and the components of the handpiece 14, which all make up the surgical device. Specifically, FIG. 5 shows the capsulotomy device with self contained suction system 2, outside of the capsulotomy cartridge shell 1. The capsulotomy cartridge reversibly fits onto one end 15 of the handpiece 14 In an embodiment, the handpiece 14 includes a mechanical slider 16, that has a mechanical feature, such as a latch 17, that engages the suction puller 12 (as shown in FIG. 4) on the expandable chamber 10 (as shown in FIG. 4). In another embodiment, the handpiece includes an actuator, such as a motor unit 18, that also uses a latch to engage the suction puller 12 (as shown in FIG. 4) on the expandable chamber 10 (FIG. 4). The handpiece has a power cord 19 extending to a power source. The actuation mechanism used to cause generation of suction includes latch 20, nonrotating leadscrew 21, and structures 22, which are described with regard to FIG. 6.

In some embodiments, the cartridge is a disposable portion that can be attachable to and detachable from the handpiece 14 to be disposed following each use and replaced with a new, sterile cartridge. The capsulotomy devices can be shipped to the surgeon within the external shell 1 as a cartridge, and can be maintained inside the external shell 1 until it is time for use on a patient. In this way, the capsulotomy device remains protected and sterile from factory all the way to use for performing a capsulotomy on a patient.

Figure 6:
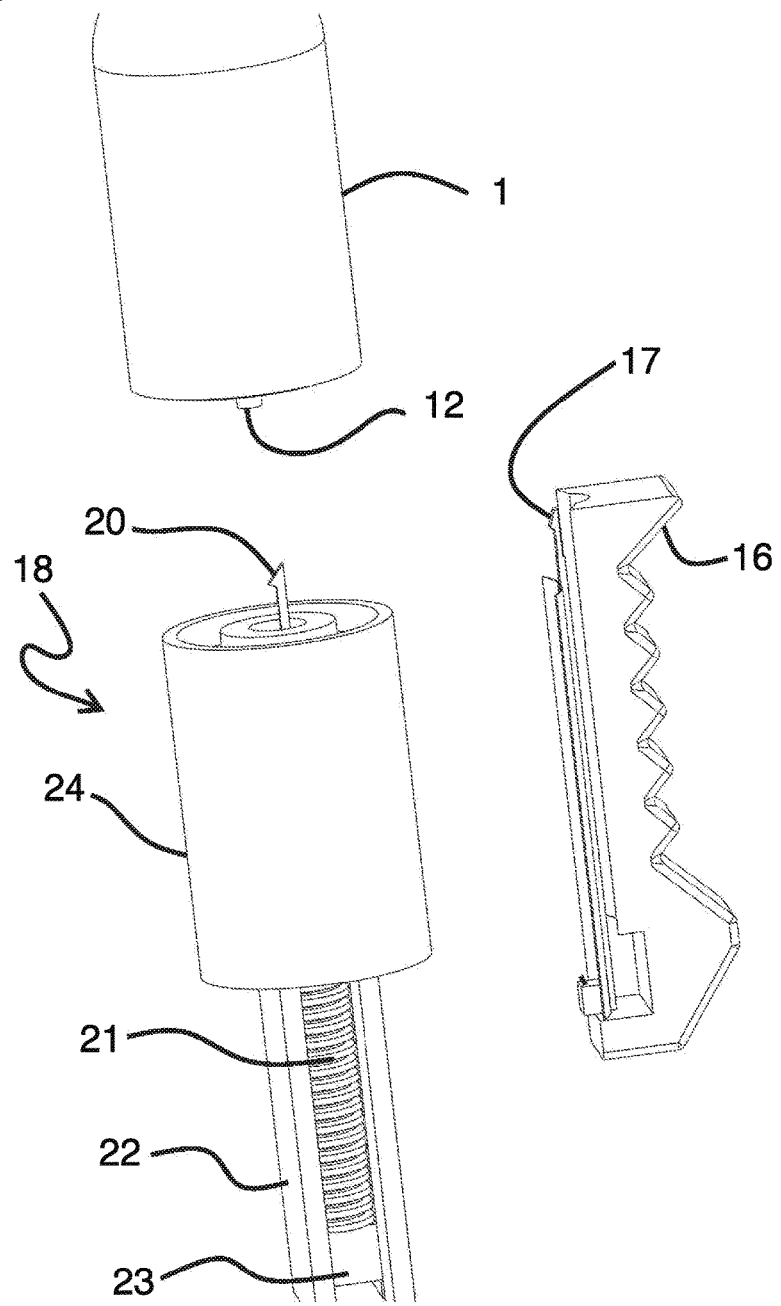
FIG. 6 illustrates a close-up view of the relationship between features on the capsulotomy cartridge and components in the handpiece, including a motor, sliding knob, according to embodiments of the invention.

FIG. 6 illustrates a close-up view of components of the capsulotomy cartridge and their relationship to components within the handpiece 14, according to an embodiment. Specifically, FIG. 6 shows a close up view of an embodiment of actuation mechanisms within the handpiece 14 for causing generation of suction within the disposable unit (e.g., the cartridge). One embodiment includes motor unit 18 for generating suction by engaging the suction puller 12 of the cartridge. The motor unit 18 in the handpiece 14 includes a latch 20 that engages suction pull 12 on the expandable chamber 10 (as shown in FIG. 4) of the capsulotomy device. The latch 20 is translated by nonrotating leadscrew 21 (structures 22 and 23 can prevent leadscrew rotation). Motor housing 24 contains the motor stator and rotor (which rotates the leadscrew nut that translates the leadscrew). Other forms of linear motion generation to expand the expandable chamber in the capsulotomy cartridge include smooth memory alloy actuators that do not require mechanical gearing to effect linear motion. In some embodiments, the components of the device shown in FIGS. 1-4 make up a disposable unit that can be reversibly attached to a handpiece, as described in reference to FIG. 5-6, such that the handpiece 14 can house the components that allow suction to be provided to the cartridge and allow actuation of the suction cup/cutting element.

FIGS. 7A-4B illustrate an optical technique for using deflection of the suction cup to verify suction status and efficiency, according to an embodiment. Specifically, FIG. 7A shows in schematic cross section an embodiment of the invention in which the suction cup 25 has been placed against the lens capsule 26, but suction has not yet been applied. The roof of the suction cup 25 has a polished region 27 that is smooth and does not scatter light. The polished region is at least partially reflective depending on the difference in refractive index between the surface of the silicone and the surrounding liquid, and acts as a mirror such that a portion of the incident light $L_I$ from the lens microscope illuminator is reflected (ray $L_R$) back up through the optical path to the eye pieces to produce a bright area. In FIG. 7B suction has been applied to the suction cup 25, and the space encompassed by the suction cup 28, is reduced. Since the polished area is located near the cutting element 29, a large angle change occurs, and reflected ray $L_R$ will not be reflected up the optical path of the surgical microscope. Thus, the area 27 will appear dark. This provides a visible signal to a surgeon or other user that the suction cup is under sufficient suction.

In an embodiment, a larger effect is achieved by applying a smooth reflective coating in area 27 (the geometry of area 27 may be a discrete spot, or a 360 degree annulus, for example) such as small glass or plastic flakes that are very thin and have a thin layer of a reflective metal, or smooth metal flakes. In a further embodiment, the reflective flakes are each between 0.5-5 microns thick and 50-150 microns in diameter. In one example, the reflective flakes are each 1 micron thick and 100 microns in diameter, and held by a silicone adhesive to the suction cup. In another embodiment, an annular array of corner cube reflectors is molded onto the roof of the suction cup 25. The reflectors are dark under suction because the distortion resulting from the suction destroys the corner cube geometry. FIG. 7B shows the radius 30 at which the roof of the suction cup transitions from contact with the capsule membrane 26, to noncontact. The location of this radius provides a reading of the suction pressure within the suction cup. When the pressure reaches a threshold value, the device can most effectively use a discharge of a pulse of electric current to cut the lens capsule. Thus, a user such as a surgeon can monitor the pressure to determine when a pulse can effectively be applied. This contact radius as a function of pressure can be controlled by the design of the stiffness of the suction cup roof, and its features.

Figure 8:
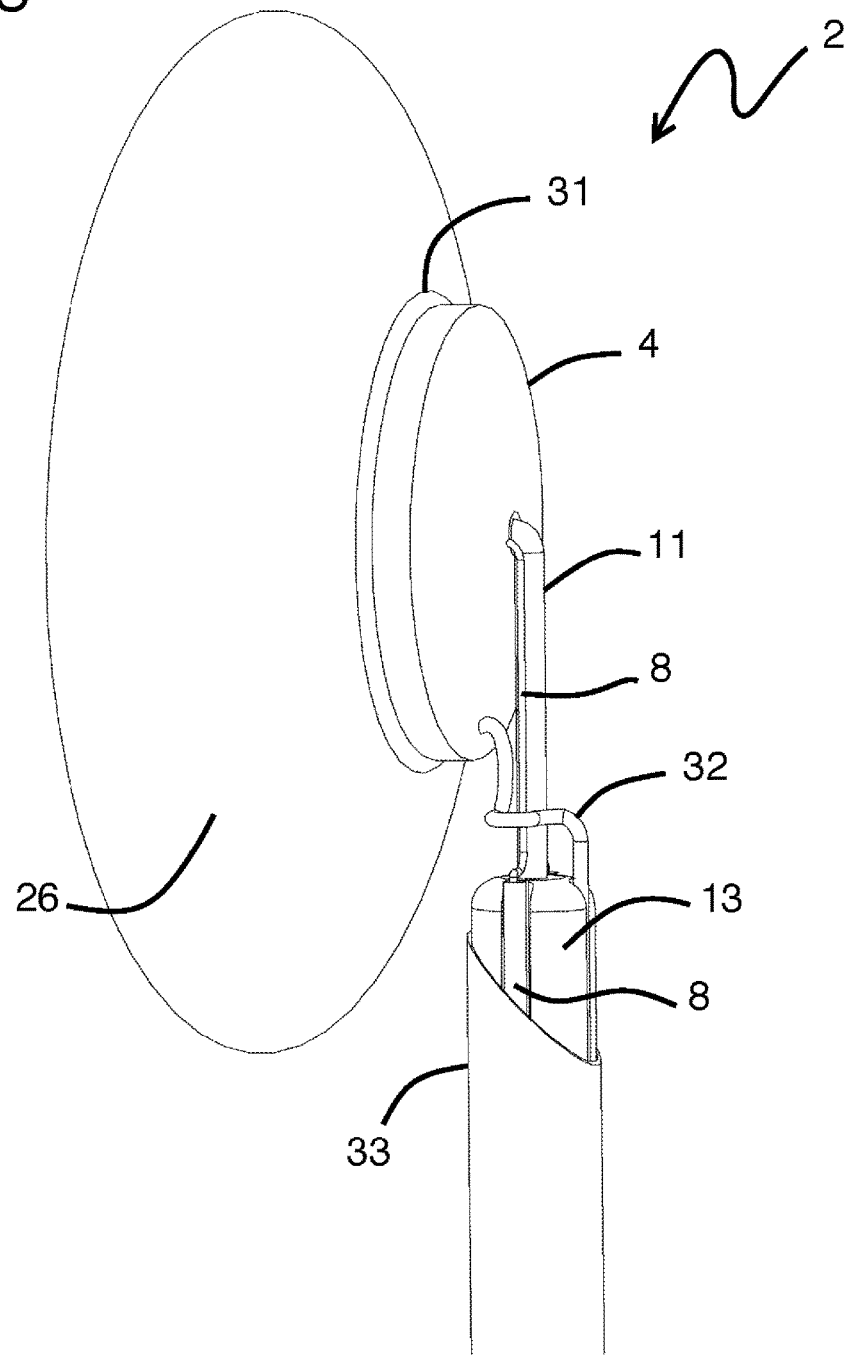
FIG. 8 illustrates a capsulotomy cartridge with the suction cup/cutting element in position for lens capsule cutting, according to an embodiment of the invention.

FIGS. 8 and 9 illustrate a capsulotomy device having a suction cup 4 with a sealing lip 31 that can form a fluidic seal against the surface of the lens capsule 26 of an eye. In an embodiment, a suction tube 11 providing a lumen for suction is attached at (or near) the center of the suction cup. The suction tube is attached to or contained within a supporting handle 13 that may include grooves to anchor electrical leads 8 (only one lead is visible in FIG. 8), and a groove to anchor and guide tether 32. The tether 32 is attached at one end to the suction cup, and at the other end attached to a slidable member of the handle 13. In FIG. 8, the tether 32 is slack with no tension. In FIG. 9 the tether 32 is under tension and not slack. In an embodiment, the handle does not include a slidable member. In this embodiment, the tether is rigid and is attached at one end to the suction cup, and at the other end to the handle. At a resting position, the tether is separated from the cutting element by a gap. When a user (such as a surgeon) pulls the device through a corneal incision to remove the device from the eye, the suction cup and handle can stretch to eliminate the gap. Thus, the tether acts as a rigid anchor that is capable of pulling the cutting element to provide necessary force to remove the device from the eye.

Enclosed within the suction cup is a circular electrical cutting element 7 (as shown in FIG. 2). Electrical leads 8 are connected to this element at positions that are separated, for example, by 180 degrees Like the suction tubes, the electrical components run through the length of the handle 13 of the capsulotomy device and can run through the length of the handpiece 14 to power cord 19.

FIG. 8 illustrates a capsulotomy device, according to one embodiment. Specifically, FIG. 8 shows the device 2, in use within the anterior chamber of an eye. In one embodiment, the device may be introduced into the anterior chamber while it is folded in an orderly manner within an inserter 33, which fits through a corneal incision. The suction cup 4 and cutting element are first compressed and stored within the inserter. Next, the inserter is inserted through a corneal incision. The suction cup and cutting element are then pushed out of the inserter 33 into the anterior chamber and assume their native shapes. The sealing lip 31 is positioned to contact the surface of the capsular membrane 26, which is the outer tissue layer encapsulating the lens of the eye. Suction is applied through the lumen of the tube 11, which is coupled to the suction cup. Next, as suction is applied, the suction cup 4 pushes a cutting element 7 (FIGS. 2, 3) against the capsular membrane of the lens. When the cutting element is in close contact with the capsular membrane over the entire 360 degrees, an electrical current is made to flow through the cutting element 7 to cut the capsular membrane. The tether 32, which serves as a mechanical connection, is attached to the suction cup 4 at one end, and at the opposite end is attached to a slidable member that slides along the long axis of the handle 13. During capsule cutting, the tether is slack to allow for sealing to occur between the suction cup and the capsule. A slack tether does not exert any force or distort the suction cup and the cutting element, and thus does not interfere with the suction cup sealing onto a capsular membrane surface. FIG. 9 illustrates a capsulotomy device in use immediately after having excised a patch of capsular membrane, according to an embodiment. Specifically, FIG. 9 shows the device as it is being moved away from the lens after the electrical discharge has occurred. The cut edge 34 of the capsulotomy is shown, and the circular or rounded patch of capsular membrane has been excised and removed by the device, leaving the surface 35 of the lens cortex exposed. The tether 32 is put under tension by sliding the slidable member along the axis of the handle 13, increasing the distance between the tether's attachment points on the suction cup and the attachment point on the slidable member. This causes the tether to be pulled taut and restricts the motion of the back end of the suction cup, where the tether is attached. As the suction cup 4 is compliant, pulling on the tether 32 will cause the back end to stretch and further pulling it closer to the handle 13 and suction tube 11 (FIG. 8), and for the suction cup, suction tube, and handle to move as one unit. This tethering of the suction cup to the handle and their unitary movement is useful as the handle and the suction cup are retracted back into the inserter 33, prior to removal of the entire capsulotomy device from the eye. In embodiments without an inserter, the tethering mechanism also allows the suction cup and handle to be simply pulled back as one unit through the corneal incision. Without the tether, the back end of the suction cup can move independently of the handle and may not find and enter the corneal incision as the handle is retracted from the eye. This will lead to the undesirable consequence of the suction cup left behind in the eye and twisting uncontrollably as it hits the inner surface of the cornea.

Corneal Incision Finder

FIG. 10 illustrates components of an embodiment of a capsulotomy device 41 including an incision finder 42 after it has been inserted into the anterior chamber 56 of an eye, and after the incision finder 42 has been withdrawn from the eye. The incision finder 42 is designed to allow the capsulotomy device to more easily enter and exit a corneal incision of the eye. The features of the incision finder 42 include the leading edge (or distal tip) 43, one or more hooks 44, and support beam 45. The leading edge 43 is shaped to facilitate entry of a cutting element (such as a cutting ring 46 or the cutting element 7 shown in prior Figures) or a combination of a cutting element and suction cup (such as suction cup 4 shown in prior Figures) through a corneal incision. In an embodiment, the leading edge extends beyond the suction cup. In another embodiment, the leading edge is formed from a sufficiently hard and sturdy material such that it can push in between the upper and lower edges of the incision of the eye. As the leading edge 43 is pushed through the incision, the cutting ring 46 is pulled into the incision by hooks of the incision finder. In some embodiments, an expandable chamber (such as a piston) is coupled to the incision finder and uses a suction source to translate the incision finder into and out of the incision. In further embodiments, this expandable chamber is coupled to an external device that generates suction and provides suction to the suction cup. Once the cutting ring has been pulled into the incision, the leading edge and the rest of the incision finder can be pulled out of the eye, leaving the cutting ring behind. In an embodiment, the support beam connects to a mechanism for translating the incision finder 42, and this translation mechanism is housed within the capsulotomy cartridge. In other embodiments, the incision finder is used to insert a cutting element through a corneal incision separate from the capsulotomy cartridge described above, and is used independent of the cartridge. Additional features of the capsulotomy device include lead wires 47 and potting tabs 57.

The mechanism by which the cutting ring 46 operates is by heating from a brief pulse of electric current (for example, 50-23 amps for 2-10 milliseconds). In FIG. 10, the cutting ring 46 is shown in a cutting position in contact with the lens capsule 49 of the eye. The diameter of the excised patch of membrane is typically 5.0-5.5 mm, but can be smaller or larger. The cutting ring enters the anterior chamber 56 through a corneal incision 51 that the surgeon makes in the cornea (50, shown in cut-away view). The corneal incision is typically 2.3-3.0 mm wide, so the circular or rounded footprint of the cutting ring is deflected into a streamlined shape as it passes through the incision. Once it is past the cornea, the cutting ring can spring back to its circular shape by virtue of its elasticity.

FIG. 11 shows the leading edge 43 of the incision finder 42 as it enters the corneal incision 51, according to an embodiment. The cutting ring 46 can be held by hooks 44 of the incision finder 42 so that the cutting ring is dragged or pulled through the corneal incision. Not shown in FIG. 2 is a suction cup which prevents the hooks 44 from contacting the cornea, and which can be made of silicone. However, in some embodiments, the suction cup is not included and the hooks 44 are coated with silicone or a protective covering is included to cover the hooks 44 to avoid contact with the cornea. The hooks 44 are designed so that during forward translation into the corneal incision, the hooks mechanically secure the cutting element and bring the cutting element through the corneal incision. The hooks 44 can slide off the cutting ring 46 when the incision finder 42 is withdrawn from the eye. Thus, the hooks 44 can simply detach from the cutting ring when the incision finder is retracted. Designs other than hooks can also be used, as well, for guiding the cutting element.

Figure 12:
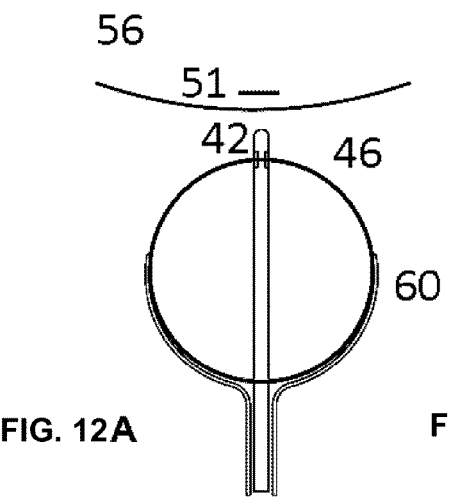
FIGS. 12A-12F illustrate an embodiment of a capsulotomy device including an incision finder where lead wires are pulled back and allow a cutting ring to achieve a streamlined shape, according to an embodiment of the invention.
Figure 12:
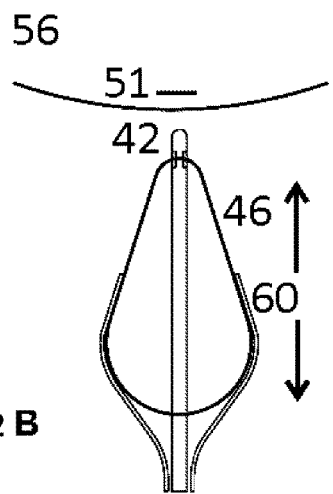
Figure 12:
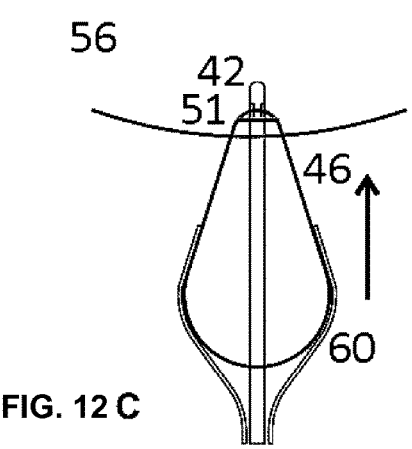
Figure 12:
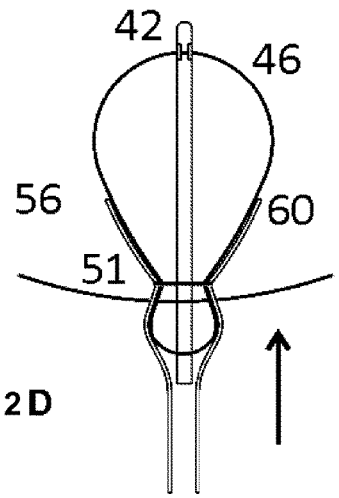

FIGS. 12A-12F show a method of pulling back lead wires 60 relative to the incision finder, according to an embodiment. This method allows lead wires 60 to be pulled back relative to the incision finder 42 so that the cutting ring 46 can achieve a streamlined shape prior to entering an incision. FIG. 12A shows an unstressed position of a capsulotomy device. FIG. 12B shows the lead wires 60 pulled back relative to the incision finder, as indicated by the vertical arrows. FIG. 12C shows the entry of the incision finder 42 through the incision 51 into the anterior chamber of the eye 56. FIG. 12D shows that tension on the lead wires 60 can be reduced to allow the cutting ring 46 to go back to a circular shape as it passes the incision. FIG. 12E shows that device fully within the anterior chamber of the eye 56 and back to the unstressed position. FIG. 12F shows that the incision finder 42 of the capsulotomy device has been fully withdrawn from the eye.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

I claim:

1. A surgical device comprising:
   a capsulotomy device comprising:
      a suction cup,
      a cutting element coupled to the suction cup in a position such that the cutting element can be put into contact with a lens capsule of an eye to excise a portion of tissue of the lens capsule, the suction cup and cutting element being collapsible, and
      an incision finder comprising a leading edge and one or more hooks, the leading edge configured for insertion through a corneal incision in the eye to an anterior chamber of the eye, the one or more hooks configured to reversibly attach to the cutting element and pull the cutting element through the corneal incision to the anterior chamber; and
   a shell structure configured for housing the capsulotomy device within, the shell structure configured to contain the suction cup, the cutting element, and the incision finder of the capsulotomy device to protect the capsulotomy device before use in performing a capsulotomy.

2. The surgical device of claim 1, wherein the surgical device is reversibly attachable to a handpiece of the surgical device, and wherein the surgical device is positionable on the handpiece such that, when the surgical device is in use for performing the capsulotomy, suction is provided to the suction cup via the suction mechanism operable through the handpiece.

3. The surgical device of claim 2, wherein the cutting element comprises a cutting ring coupled to one or more electrical leads extendable from the surgical device and through the handpiece.

4. The surgical device of claim 3, further comprising a handle coupled to the suction cup and the surrounding the one or more electrical leads, and further comprising a tube extending through the handle and providing the fluid communication between the suction cup and the chamber.

5. The surgical device of claim 1, further comprising a suction generator coupled to the chamber, the suction generator configured to be actuated to expand the chamber to create the suction provided to the suction cup.

6. The surgical device of claim 5, wherein the suction mechanism further comprises an actuator shaped to engage the suction generator to pull the suction generator proximally such that the chamber expands to provide the suction.

7. The surgical device of claim 6, wherein the actuator is a motor unit.

8. The surgical device of claim 1, wherein the cutting element comprises a cutting ring coupled to a first electrical lead and a second electrical lead, the first and second electrical leads located 180 degrees apart from each other around an edge of the cutting ring.

9. The surgical device of claim 1, the suction cup further comprising a sealing lip around an edge of the suction cup, the cutting element mounted to an underside of the suction cup around the edge internal to the sealing lip, wherein the cutting element is positioned to contact the portion of tissue of a lens capsule when suction is applied by the suction cup to seal the sealing lip to the lens capsule.

10. The surgical device of claim 1, wherein the cutting element is circular.

11. The surgical device of claim 1, wherein the chamber is a flexible bulb or a piston structure.

12. The surgical device of claim 1, wherein a roof of the suction cup comprises a reflective coating.

13. The surgical device of claim 12, wherein the reflective coating comprises metal flakes, glass flakes, or plastic flakes.

14. The surgical device of claim 1, further comprising:
   a handle coupled to the suction cup; and
   a tether having a first end and a second end, the first end coupled to the handle, and the second end coupled to the suction cup.

15. The surgical device of claim 1, further comprising a suction tube attached to the suction cup, the suction tube configured to draw in fluid from the suction cup through the suction tube when suction is provided to the suction cup.

16. The surgical device of claim 1, the shell structure further comprising an inserter tip having an opening on a distal end, the inserter tip configured for insertion of the distal end through a corneal incision in the eye, the inserter tip shaped to contain the suction cup and the cutting element of the capsulotomy when collapsed and to allow the suction cup and cutting element to be inserted through the corneal incision into an anterior chamber of the eye.

17. The surgical device of claim 16, wherein the suction cup and the cutting element are configured to translate through the opening on the distal end of the inserter tip into the anterior chamber of the eye when the inserter tip is inserted through the corneal incision in the eye.

18. The surgical device of claim 1, wherein the incision finder is capable of withdrawing at least in part from the anterior chamber through the corneal incision whereby the cutting element remains in the anterior chamber, and wherein the one or more hooks are configured to detach from the cutting element when the incision finder is in the anterior chamber.

19. The surgical device of claim 1, wherein the cutting element is composed of a flexible material, and wherein the cutting element is configured to be circular while in a relaxed position and oblong while the one or more hooks pull the cutting element through the corneal incision.

20. The surgical device of claim 1, wherein the incision finder is coupled to the expandable chamber, the expandable chamber coupled to an external device that generates suction to translate the incision finder into and out of the incision.

21. The surgical device of claim 1, wherein the capsulotomy device further comprises:

a chamber in fluid communication with the suction cup, the chamber configured to provide suction to the suction cup via a suction mechanism operable through a handpiece.

\* \* \* \* \*

UNITED STATES PATENT AND TRADEMARK OFFICE
CERTIFICATE OF CORRECTION

PATENT NO. : 10,070,989 B2
APPLICATION NO. : 14/613112
DATED : September 11, 2018
INVENTOR(S) : Christopher Guild Keller It is certified that error appears in the above-identified patent and that said Letters Patent is hereby corrected as shown below:

In the Claims

Column 11, Line 53, Claim 2, delete "the suction mechanism" and insert --a suction mechanism--

Column 11, Line 60, Claim 4, delete "and the surrounding" and insert --and surrounding--

Column 11, Lines 62-63, Claim 4, delete "the fluid communication" and insert --fluid communication--

Column 11, Line 67, Claim 5, delete "create the suction" and insert --create suction--

Column 12, Line 17, Claim 9, delete "of a lens capsule" and insert --of the lens capsule--

Signed and Sealed this
Ninth Day of April, 2019

Andrei Iancu
*Director of the United States Patent and Trademark Office*